United States Patent [19]
Barbut

[11] Patent Number: 6,165,199
[45] Date of Patent: Dec. 26, 2000

[54] MEDICAL DEVICE FOR REMOVING THROMBOEMBOLIC MATERIAL FROM CEREBRAL ARTERIES AND METHODS OF USE

[75] Inventor: Denise Barbut, New York, N.Y.

[73] Assignee: CoAxia, Inc., New York, N.Y.

[21] Appl. No.: 09/228,718

[22] Filed: Jan. 12, 1999

[51] Int. Cl.$^7$ ..................................................... A61B 17/00
[52] U.S. Cl. ........................ 606/200; 606/192; 606/159; 604/22
[58] Field of Search ..................................... 606/200, 192, 606/194, 195, 159, 160; 604/96, 97, 101, 19, 22

[56] References Cited

U.S. PATENT DOCUMENTS

| | | | |
|---|---|---|---|
| 4,646,736 | 3/1987 | Auth | 606/200 |
| 5,242,460 | 9/1993 | Klein et al. | 606/159 |
| 5,908,407 | 6/1999 | Frazee et al. | 606/194 |
| 5,928,192 | 9/1999 | Maahs | 606/194 |

*Primary Examiner*—Michael Buiz
*Assistant Examiner*—Lien Ngo
*Attorney, Agent, or Firm*—Lyon & Lyon LLP

[57] ABSTRACT

The invention provides a medical device having an elongate catheter, a balloon occluder mounted on a distal end of the catheter, and optionally a chopping mechanism associated with an aspiration port of the catheter. Continuous or intermittent suction can be applied to the aspiration port which is distal to the occluder to dislodge thromboembolic material in a carotid or cerebral artery. Oxygenated blood or other fluid, which may be hypothermic, can be perfused through at least one perfusion port proximal to the occluder to maintain and augment perfusion of the collateral vasculature proximal to the occlusive lesion. The flow rate of blood or fluid can be controlled by rotating two cylindrical members. Neuroprotective agents or t-PA can also be infused distal to the occluder through the aspiration port or an infusing port. Methods of using the devices in treating patients with acute stroke or occlusive cerebrovascular disease are also disclosed.

29 Claims, 11 Drawing Sheets

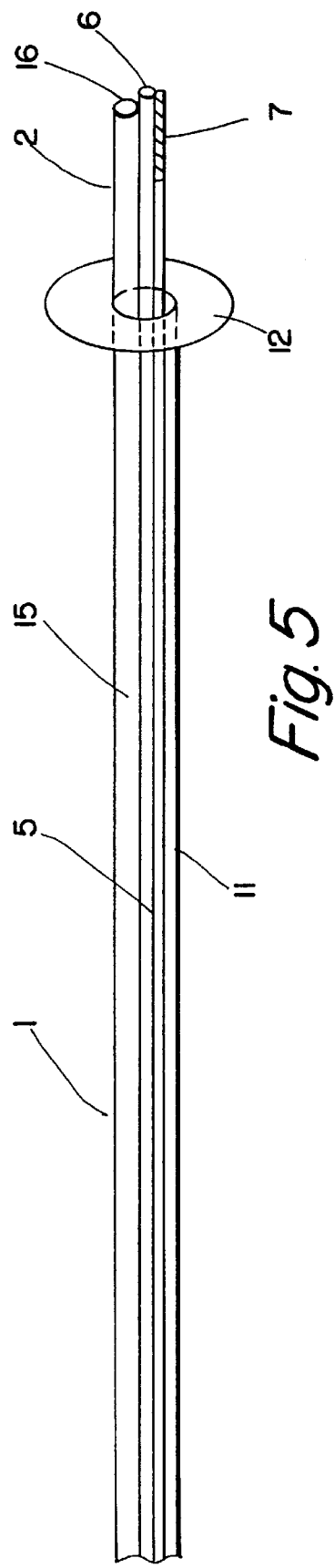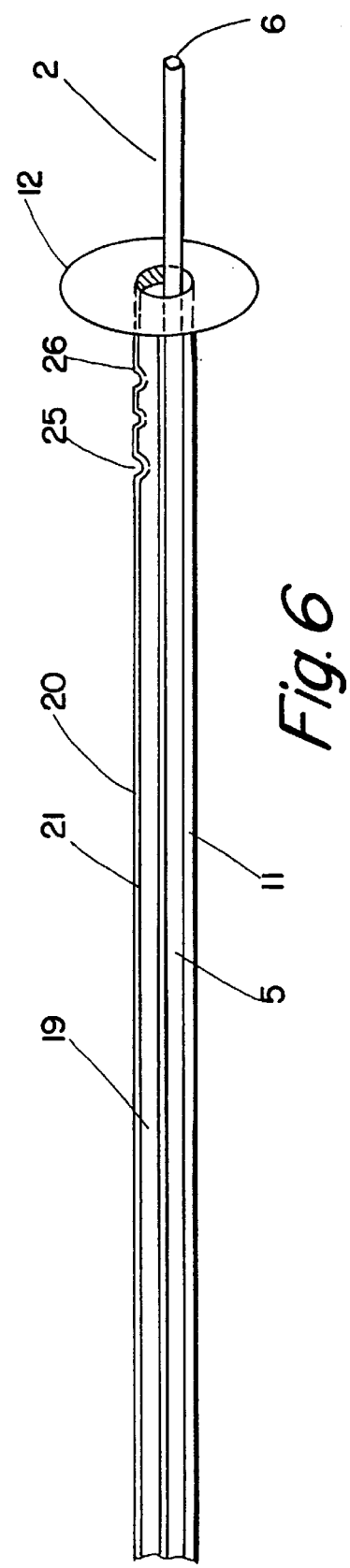

MEDICAL DEVICE FOR REMOVING THROMBOEMBOLIC MATERIAL FROM CEREBRAL ARTERIES AND METHODS OF USE

FIELD OF THE INVENTION

The present invention generally relates to medical devices useful in treating patients with acute stroke or occlusive cerebrovascular disease. More specifically, the invention provides an extra/intracranial balloon occlusive device with suction to remove a thrombus or embolus lodged in a cerebral vessel and a means of maintaining and augmenting perfusion of the collateral vasculature proximal to the offending lesion. The device may employ a chopping mechanism, vasodilator, hypothermic perfusion or local administration of t-PA and optionally an extracorporeal pumping mechanism to remove a vascular occlusion and reestablish cerebral perfusion.

BACKGROUND OF THE INVENTION

Stroke is the third most common cause of death in the United States and the most disabling neurologic disorder. Approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. Its incidence increases with age. Risk factors for stroke include systolic or diastolic hypertension, hypercholesterolemia, cigarette smoking, heavy alcohol consumption, and oral contraceptive use.

Hemorrhagic stroke accounts for 20% of the annual stroke population. Hemorrhagic stroke often occurs due to rupture of an aneurysm or arteriovenous malformation bleeding into the brain tissue, resulting in cerebral infarction. The remaining 80% of the stroke population are ischemic strokes and are caused by occluded vessels that deprive the brain of oxygen-carrying blood. Ischemic strokes are often caused by emboli or pieces of thrombotic tissue that have dislodged from other body sites or from the cerebral vessels themselves to occlude in the narrow cerebral arteries more distally. When a patient presents with neurological symptoms and signs which resolve completely within 1 hour, the term transient ischemic attack (TIA) is used. Etiologically, TIA and stroke share the same pathophysiologic mechanisms and thus represent a continuum based on persistence of symptoms and extent of ischemic insult.

When a patient presents with neurological deficit, a diagnostic hypothesis for the cause of stroke can be generated based on the patient's history, a review of stroke risk factors, and a neurologic examination. If an ischemic event is suspected, a clinician can tentatively assess whether the patient has a cardiogenic source of emboli, large artery extracranial or intracranial disease, small artery intraparenchymal disease, or a hematologic or other systemic disorder. A head CT scan is often performed to determine whether the patient has suffered an ischemic or hemorrhagic insult. Blood would be present on the CT scan in subarachnoid hemorrhage, intraparenchymal hematoma, or intraventricular hemorrhage.

Traditionally, emergent management of acute ischemic stroke consists of mainly general supportive care, e.g. hydration, monitoring neurological status, blood pressure control, and/or anti-platelet or anti-coagulation therapy. In June 1996, the Food and Drug Administration approved the use of Genentech Inc.'s thrombolytic drug, tissue plasminogen activator (t-PA) or Activase ®, for treating acute stroke. In a randomized, double-blind trial, the National Institute of Neurological Disorders and t-PA Stroke Study, there was a statistically significant improvement in stoke scale scores at 24 hours in the group of patients receiving intravenous t-PA within 3 hours of the onset of an ischemic stroke. Since the approval of t-PA, an emergency room physician could, for the first time, offer a stroke patient an effective treatment besides supportive care.

However, treatment with systemic t-PA is associated with increased risk of intracerebral hemorrhage and other hemorrhagic complications. Patients treated with t-PA were more likely to sustain a symptomatic intracerebral hemorrhage during the first 36 hours of treatment. The frequency of symptomatic hemorrhage increases when t-PA is administered beyond 3 hours from the onset of a stroke. Besides the time constraint in using t-PA in acute ischemic stroke, other contraindications include the following: if the patient has had a previous stroke or serious head trauma in the preceding 3 months, if the patient has a systolic blood pressure above 185 mm Hg or diastolic blood pressure above 110 mmHg, if the patient requires aggressive treatment to reduce the blood pressure to the specified limits, if the patient is taking anticoagulants or has a propensity to hemorrhage, and/or if the patient has had a recent invasive surgical procedure. Therefore, only a small percentage of selected stroke patients are qualified to receive t-PA.

New devices and methods are thus needed in treating patients with acute ischemic stroke and occlusive cerebrovascular disease, in treating symptomatic patients with embolization or hemodynamic compromise, or in stroke prevention, e.g., patients with incidental finding of asymptomatic carotid lesion, which improve a patient's eurological function and quality of life without causing significant side effect, and can be used in patients with contraindication to using t-PA.

SUMMARY OF THE INVENTION

The invention provides devices and methods for treatment of acute ischemic stroke and occlusive cerebrovascular disease by taking advantage of the collateral cerebral circulation. Anastomoses between the cerebral arteries provide alternative pathways in which blood can reach a given region of the brain besides the predominant supplying artery. At the base of the brain close to the sella turcica, circulus arteriosus cerebri, or circle of Willis, connects the vertebral and internal carotid arteries to each other and to the vessels of the opposite side. When occlusion of a blood vessel interrupting the flow of blood to a specific region of the brain occurs, survival of the brain tissue and therefore severity of a patient's neurological deficit depend on the number and size of its collateral arteries. The devices of the present invention utilize pressure generated by collateral cerebral circulation to facilitate removal of thromboembolic material in an occluded carotid or cerebral artery.

A first embodiment of the medical device comprises an elongate catheter, a balloon occluder, and a chopping mechanism. The catheter has a proximal end, a distal end and a lumen which communicates with an aspiration port at the distal end. The balloon occluder, which communicates with an inflation lumen and may comprise an elastomeric balloon, is mounted on the distal end of the catheter proximal to the aspiration port. The chopping mechanism is operated to chop away any particulate matter engaged by suction through the aspiration port.

In another embodiment, the catheter has an additional lumen which communicates with a port distal to the balloon occluder for infusing blood and pharmaceutical agents, such as a vasodilator or t-PA. Vasodilator, such as nifedipine or nitroprusside, is used to reverse any vascular spasm which occurs as a result of instrumentation. The chopping mechanism may comprise an abrasive grinding surface or a rotatable blade which operates within a housing, as described in Barbut et al., U.S. Pat. No. 5,662,671, incorporated herein by reference in its entirety.

In still another embodiment, the catheter includes a perfusion lumen which communicates with one or a plurality of perfusion ports and is adapted for infusion of oxygenated blood. The perfusion ports may be located on two cylindrical members which can be rotated relative to each other so that maximum blood flow through the catheter is achieved when the perfusion ports on the two members are aligned. Alternatively, the two cylindrical members can be rotated so that the perfusion ports on the two members are partially aligned to limit blood flow, or completely misaligned to achieve no blood flow. In this manner, the flow rate of blood or fluid through the perfusion ports can be varied by controlling the rotation of the two cylindrical members.

In still another embodiment, a manometer is mounted distal to the balloon occluder to monitor pressure within the chamber created by the inflated occluder and the embolic or thromboembolic occlusion.

In still another embodiment, a second balloon occluder is mounted on the catheter proximal to the perfusion ports. The second occluder, when inflated, reduces run-off of oxygenated blood from the perfusion ports back down into the aorta, thereby improving perfusion to the ischemic area by collateral circulation.

The invention also provides methods for removing atheroma from an extracranial or intracranial cerebral artery in a patient with occlusive cerebrovascular disease using the devices described above. The methods can be used to treat a wide spectrum of patients, including patients who are symptomatic due to embolization of a cerebral artery lesion or hemodynamic compromise caused by the lesion and asymptomatic patients who are found incidentally to have the lesion during nonneurological procedures such as cardiac catheterization and/or angiogram.

In a first method, the distal end of the catheter is inserted through an incision on a peripheral artery, such as a femoral artery, and advanced into the symptomatic carotid or cerebral artery. The site of vessel occlusion is localized with an angiogram or intravascular ultrasound (IVUS). In an emergency, the catheter can also be inserted into the patient's carotid artery as a direct stick after localizing the occlusion with the assistance of IVUS or standard carotid doppler and transcranial doppler (TCD). The distal end of the catheter can be advanced as far as the occlusion which could be in the common carotid artery, internal carotid artery, middle cerebral artery, anterior cerebral artery, carotid siphon, terminal internal carotid artery, or any other part of the cerebral vasculature. After the distal end of the catheter is positioned proximal to the occluding lesion, the balloon occluder is inflated to occlude the arterial lumen, thereby creating a closed chamber between the balloon and the thromboembolic occlusion. A pressure differential is created since the pressure within the chamber is lower than the pressure distal to the occlusion. Using the balloon occlusion therefore enhances contralateral hemispheric blood flow, helping to reverse the flow across the Circle of Willis, thereby providing retrograde arterial collateral enhancement to the ischemic area distal the occlusion. The catheter is attached to a vacuum and a negative pressure is applied to the aspiration port. Blood within the chamber may be completely aspirated. With continued suction, the thromboembolic materials engaged by the aspiration port under negative pressure. Occlusion of the port by the thromboembolic material and activation of the chopper mechanism thereby removes at least a portion of the occluding material.

In another method, intermittent suction is used instead of the continuous suction. The alternating negative-positive pressure gradient may dislodge the atheroma onto the aspiration port. The chopping mechanism subsequently removes the atheroma.

In still another method, after the distal end of the catheter is inserted and the occluder is inflated proximal to the intracranial or carotid occlusion, pulsatile or continuous perfusion is initiated through at least one perfusion port proximal to the occluder. In this manner, perfusion to the ischemic area distally is improved by opening and recruiting collateral vessels which supply the ischemic territory, thereby providing antegrade collateral enhancement. The more distal the occlusion in the cerebral circulation, the larger the number of collateral arteries available for recruitment by the proximal perfusion. Flow rate through the perfusion ports is adjusted by rotation of two cylindrical members of the catheter. As a result of increased perfusion distal to the occlusion, the pressure differential across the occlusive site increases, thereby facilitating dislodgment of the thromboembolic material onto the aspiration port. The atheroma is then removed under vacuum as the catheter is withdrawn, by a chopping mechanism, an atherectomy device coupled to the aspiration port, or by local administration of t-PA through an additional perfusion lumen distal to the occluder.

It will be understood that there are several advantages in using the devices and methods disclosed herein for management of acute stroke. For example, the devices can be used (1) in a majority of stroke patients, including those with contraindication to using systemic t-PA, (2) to administer neuroprotective agents and t-PA locally into an occluded vessel, thereby providing greater local benefit and fewer systemic side effects, (3) to infuse hypothermic fluid or blood to the ischemic area, thereby providing protective focal hypothermia, (4) with standard atherectomy to remove remaining arterial atheroma, (5) as an angioplasty device by inflating the balloon over the stenotic arterial lumen to enlarge the luminal diameter, (6) in other vascular procedures, such as in treatment of occlusive peripheral vascular disease, (7) by any invasive radiologist or cardiologist, (8) in the angiogram suite available in most hospitals, (9) in treating acute stroke patients with few systemic side effects, (10) to treat asymptomatic high grade stenotic lesions found incidentally, e.g., during cardiac catheterization and/or angiogram, (11) to treat symptomatic vertebral artery occlusion, and (12) to maintain perfusion to the distal ischemic area, even without removal of the occlusion, to minimize neurologic damage while alternative intervention is being considered.

BRIEF DESCRIPTION OF THE DRAWINGS

FIG. 5 depicts another embodiment of the device for treatment of acute stroke.

FIG. 6 depicts another embodiment of the device having perfusion ports proximal to the balloon occluder.

DETAILED DESCRIPTION

The cerebral circulation is regulated in such a way that a constant total cerebral blood flow (CBF) is generally maintained under varying conditions. For example, a reduction in flow to one part of the brain, such as in acute stroke, may be compensated by an increase in flow to another part, so that CBF to any one region of the brain remains unchanged. More importantly, when one part of the brain becomes ischemic due to a vascular occlusion, the brain compensates by increasing blood flow to the ischemic area through its collateral circulation.

Figure 1:
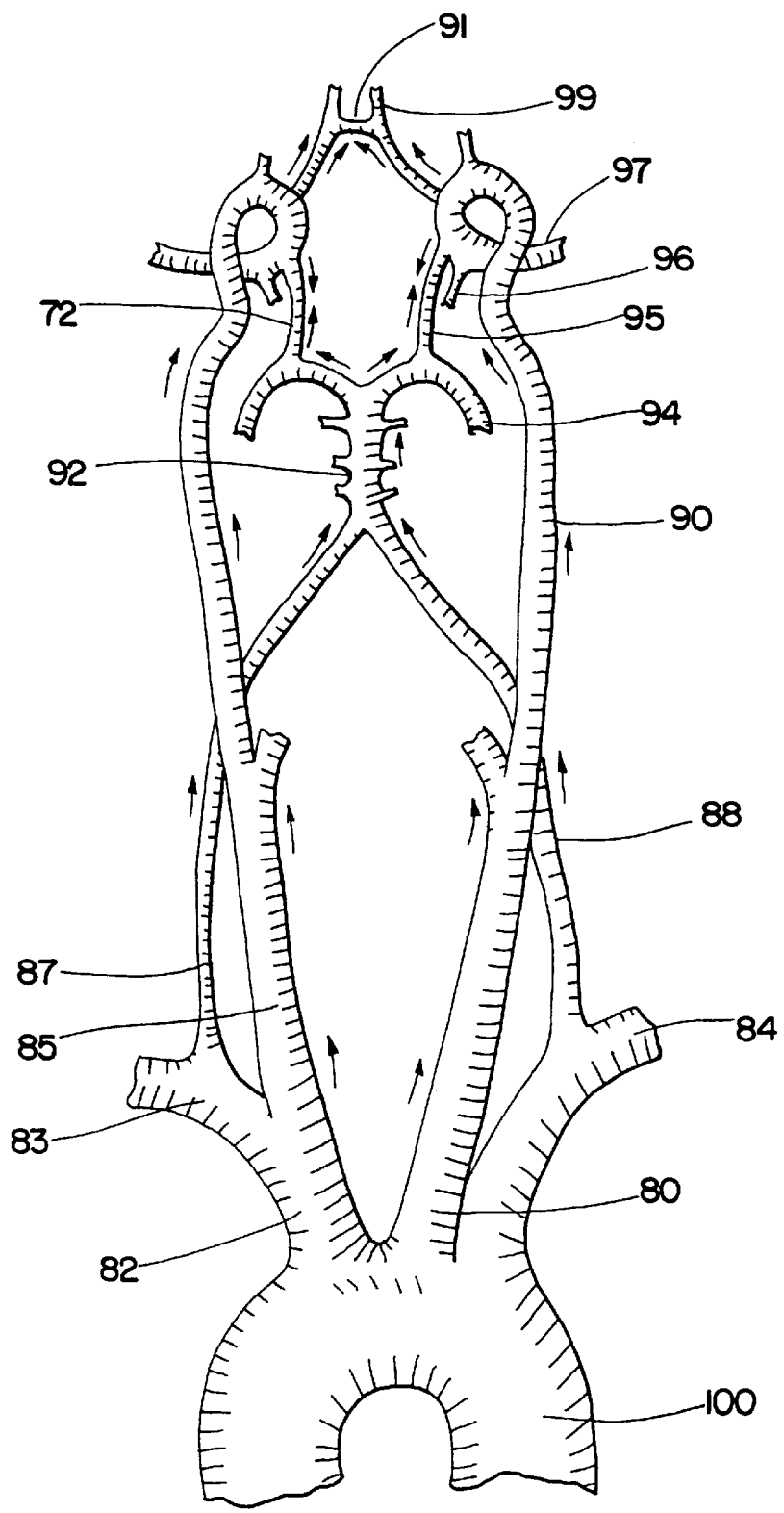
FIG. 1 depicts a normal cerebral circulation in the Circle of Willis.

FIG. 1 depicts a normal cerebral circulation and formation of Circle of Willis. Aorta 100 gives rise to right brachiocephalic trunk 82, left common carotid artery (CCA) 80, and left sub clavian artery 84. The brachiocephalic artery further branches into right common carotid artery 85 and right subclavian artery 83. The left CCA gives rise to left internal carotid artery (ICA) 90 which becomes left middle cerebral artery (MCA) 97 and left anterior cerebral artery (ACA) 99. Anteriorly, the Circle of Willis is formed by the internal carotid arteries, the anterior cerebral arteries, and anterior communicating artery 91 which connects the two ACAs. The right and left ICA also send right posterior communicating artery 72 and left posterior communicating artery 95 to connect, respectively, with right posterior cerebral artery (PCA) 74 and left PCA 94. The two posterior communicating arteries and PCAs, and the origin of the posterior cerebral artery from basilar artery 92 complete the circle posteriorly.

Figure 2:
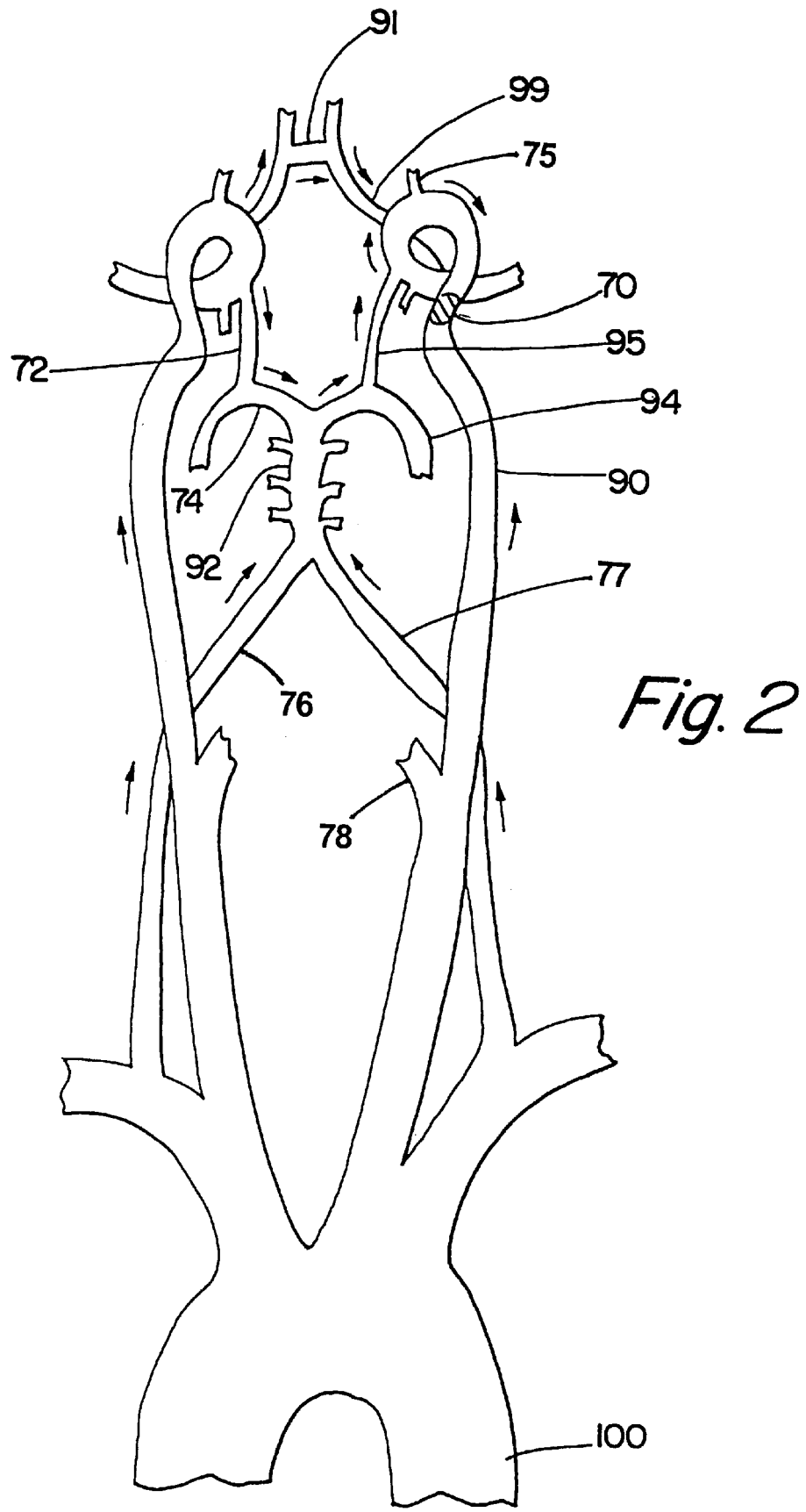
FIG. 2 depicts a reversed circulation in the Circle of Willis to compensate for an occlusion in the left carotid siphon artery.

When an occlusion occurs acutely, for example, in left carotid siphon 70, as depicted in FIG. 2, blood flow in the right cerebral arteries, left external carotid artery 78, right vertebral artery 76, and left vertebral artery 77 increases, resulting in directional change of flow through the Circle of Willis to compensate for the sudden decrease of lood flow in the left carotid siphon. Specifically, blood flow reverses in right posterior communicating artery 72, right PCA 74, left posterior communicating artery 95. Anterior communicating artery 91 opens, reversing flow in left ACA 99, and flow increases in the left external carotid artery, reversing flow along left ophthalmic artery 75, all of which contribute to flow in left ICA 90 distal the occlusion to provide perfusion to the ischemic area distal to the occlusion.

Figure 3:
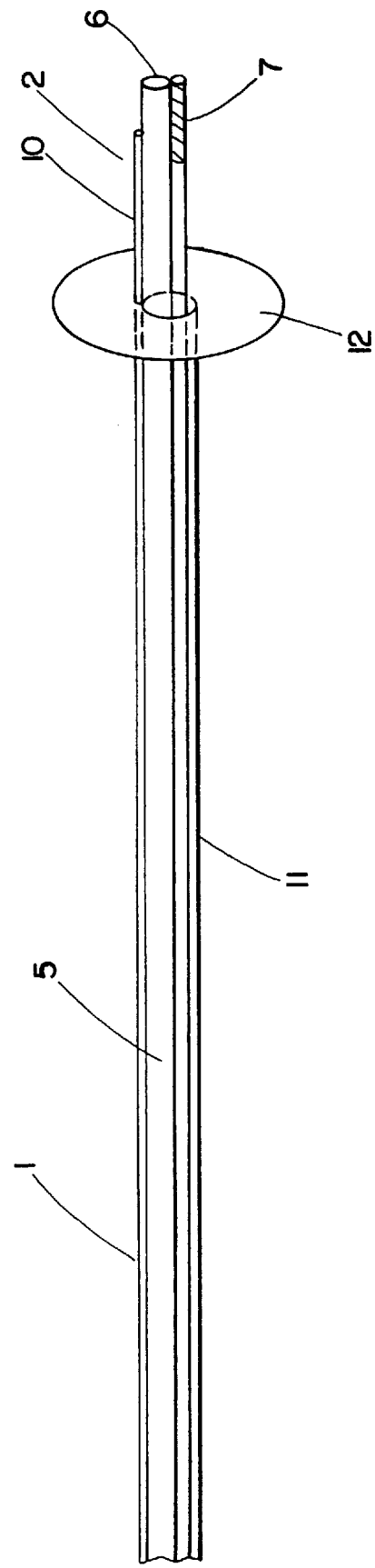
FIG. 3 depicts an embodiment of the medical device for treatment of acute stroke according to the present invention.

FIG. 3 depicts an embodiment of the medical devices for treatment of acute stroke or symptomatic occlusive disease according to the present invention. The device comprises catheter 1, which has a proximal end (not shown), distal end 2, and lumen 5. Lumen 5 communicates with the proximal end, adapted for attachment to a vacuum, and distally to aspiration port 6. The lumen may also be adapted for infusion of blood, fluid, or pharmaceutical agent, such as a vasodilator. Balloon occluder 12, communicating with inflation lumen 11, is mounted on distal end 2 of the catheter proximal to aspiration port 6. The device further comprises chopping mechanism 7 which is closely associated with the aspiration port, so that occlusion of the aspiration port by any material will activate the chopping mechanism. Manometer 10 is also mounted on the distal end of the catheter distal to balloon occluder 12 for monitoring pressure distal to the occluder. It will be understood that balloon occluder 12 in FIG. 3 and in all other embodiments described herein can be substituted for any other expandable occlusive device, e.g., a pair of nested cones rotatable relative to one another, and each having a plurality of holes which pass into and out of alignment during such rotation. Such a system of nested cones is described in greater detail in Barbut, U.S. App. Serial No. [Lyon & Lyon Docket No. 239/132], incorporated herein by reference.

Figure 4A:
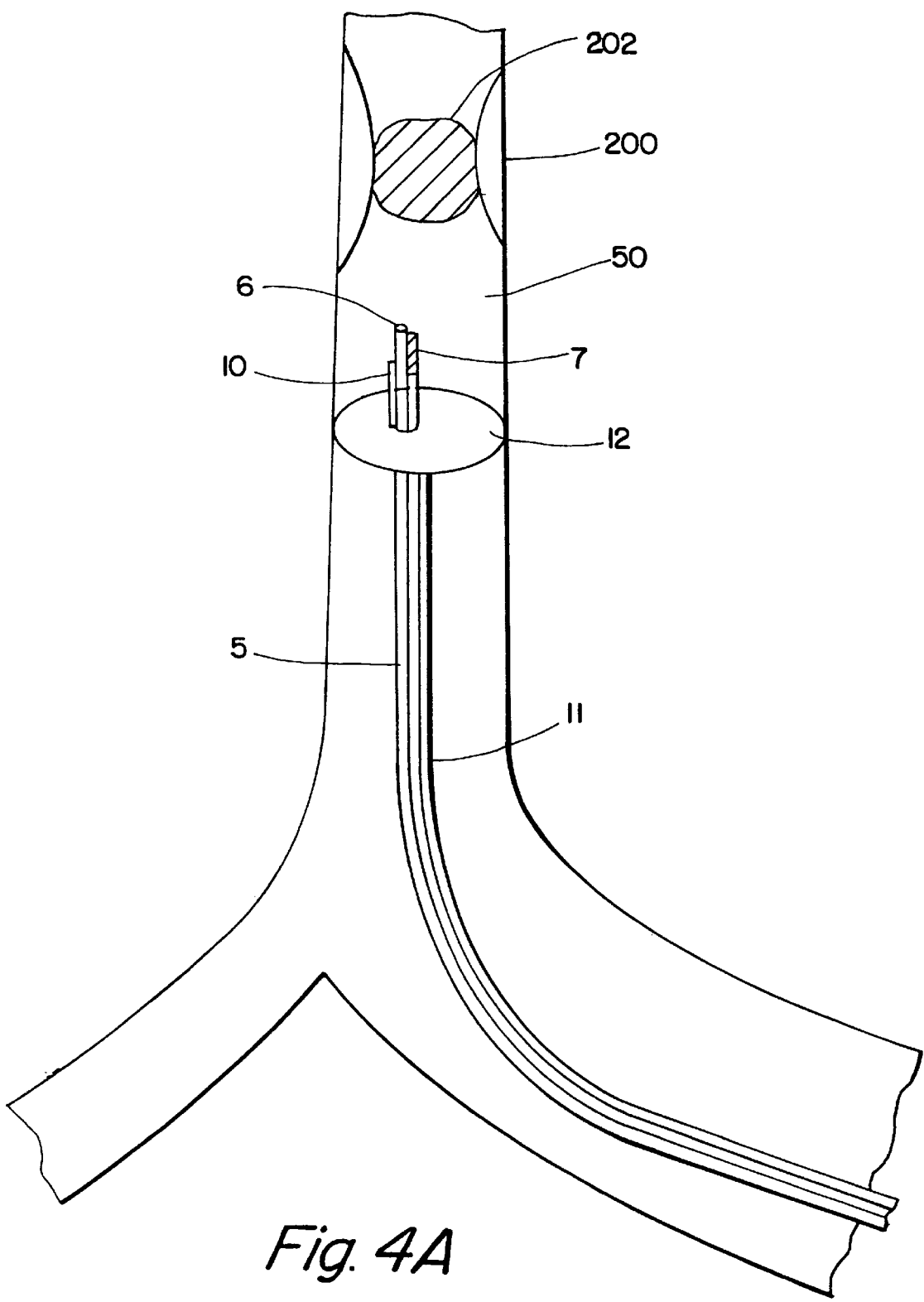
FIG. 4A depicts the device of FIG. 3 inserted proximal to an occlusive lesion.
Figure 4B:
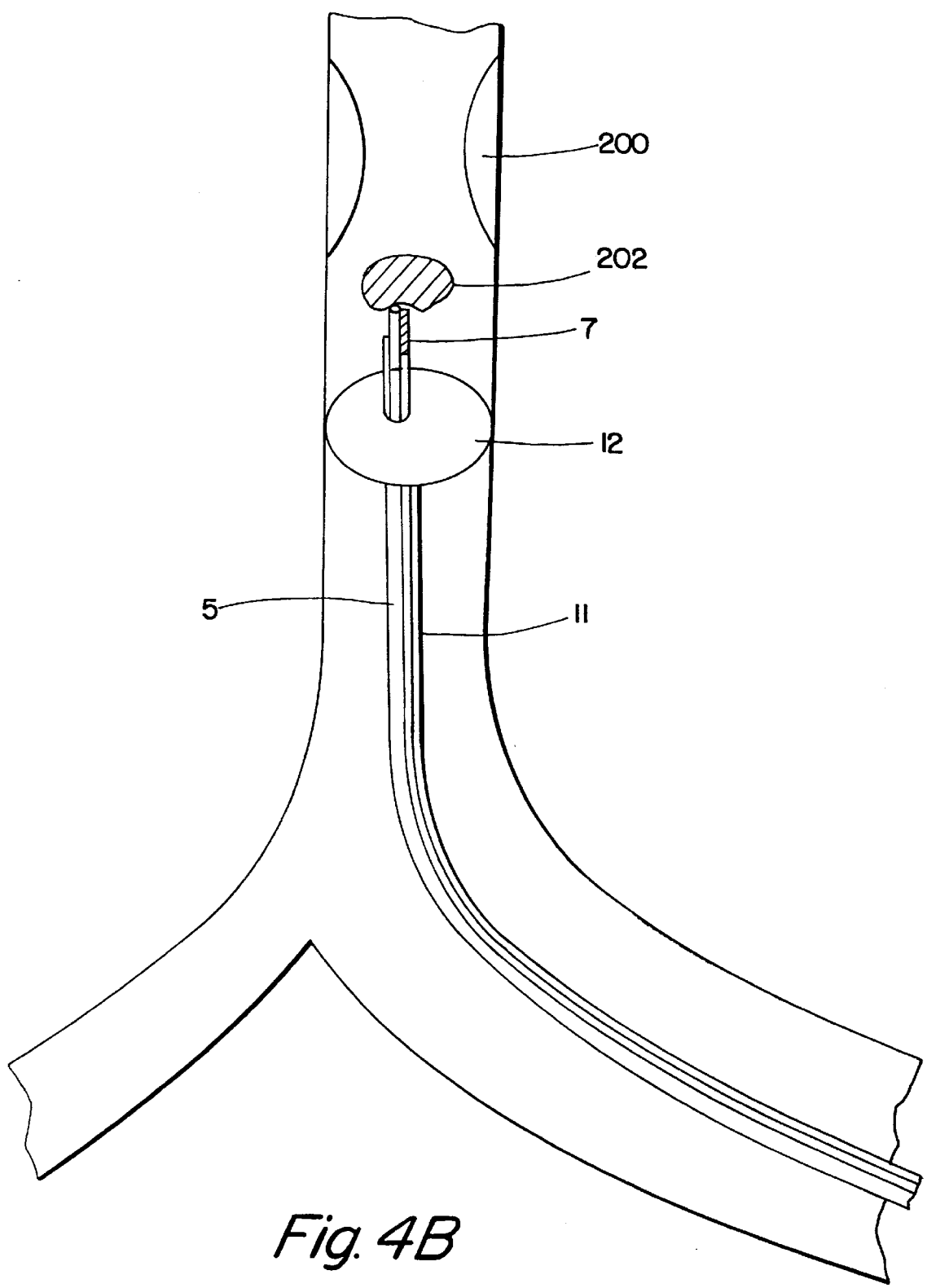
FIG. 4B depicts thromboembolic material being removed by the device shown in FIG. 3.

In use, the distal end of the catheter is inserted through an incision on a peripheral artery into a more distal carotid or intracranial artery, such as the terminal ICA, carotid siphon, MCA, or ACA as depicted in FIG. 4A. Thromboembolic material 202 is shown occluding the lumen of a cerebral artery narrowed by atheromatous plaque 200. The occlusion site can be localized with cerebral angiogram or IVUS. In emergency situations, the catheter can be inserted directly into the symptomatic carotid artery after localization of the occlusion with the assistance of IVUS or standard carotid doppler and TCD. Balloon occluder 12 is then positioned approximately 1 to 3 cm proximal to the thromboembolic occlusion and inflated to occlude the arterial lumen. Closed chamber 50 is created between occluder 12 and thromboembolic occlusion 202. A vasodilator, e.g., nifedipine or nitroprusside, may be injected through lumen 5 and port 6 to reverse vascular spasm induced as a result of instrumentation and to reduce pressure in the closed chamber. Pressure within the chamber is monitored by manometer 10 and can be altered by applying vacuum to the proximal end of the catheter. A pressure dial, which may be included in the proximal end of the catheter, allows suction within the chamber to be regulated according to the vessel size cannulated. With suction, blood is initially aspirated from chamber 50. When continuous negative pressure is applied, occluding material 202 is dislodged onto and occludes aspiration port 6, thereby activating chopping mechanism 7 to remove the occlusion, as depicted in FIG. 4B. Blood can then be perfused through lumen 5 and port 6 to determine the extent of reperfusion distal to the occluded site.

If the occlusion is not removed by the above continuous suction method, intermittent suction can be used to create an alternating negative-positive pressure gradient, which may dislodge the thromboembolic occlusion. Alternatively, a thrombolytic agent, e.g., t-PA may be infused through lumen 5 and port 6 to lyse the occlusion if soft thrombus is suspected. Standard atherectomy or angioplasty with or without stent placement can also be performed on atheromatous plaque 200 after removal of the occlusion if perfusion through the diseased artery is still inadequate. Balloon occluder 12 can be used as an angioplasty balloon to enlarge the luminal diameter of the stenotic artery, thereby establishing reperfusion.

FIG. 5 depicts another embodiment of the device. Catheter 1 has a proximal end adapted for attachment to a vacuum, distal end 2, and lumen 5 which communicates with aspiration port 6. Balloon 12 is mounted on distal end 2 and communicates with inflation lumen 11. Chopping mechanism 7 is closely associated with aspiration port 6 to remove any material occluding the port. The device further comprises infusion lumen 15, which communicates with port 16, for infusion of fluid, blood, or pharmaceutical agent.

In use, distal end 2 of the catheter is inserted into a carotid or cerebral artery as described above in the method of using the device of FIG. 3. Balloon occluder 12 is inflated proximal to an occlusion. The balloon occlusion may improve contralateral blood flow to the distal ischemic area by reversing blood flow across the Circle of Willis. In incomplete occlusive lesions or partially removed occlusions, retrograde arterial flow distal the occlusion can further be improved by infusing a vasodilator through lumen 15 and port 16. Vasodilatation distal to the balloon occluder reduces pressure within the closed chamber and increases the pressure differential across the occlusion. Lumen 15 and port 16 can also be used to infuse t-PA to lyse the occlusion or perfuse blood or other fluid distally after the occlusion is removed by suction and chopping mechanism 7.

FIG. 6 depicts still another embodiment of the device having perfusion ports proximal the balloon occluder. The device comprises a catheter, perfusion lumen 19, and balloon occluder 12, which is mounted on distal end 2 of the catheter and communicates with inflation lumen 11. The catheter has a proximal end (not shown), distal end 2, and lumen 5, which communicates with port 6. The proximal end and the lumen are adapted for aspiration or infusion of fluid or blood. Perfusion lumen 19 has two concentric cylindrical members and communicates with 1, 2, 3, 4, 5, 6, or other number of perfusion ports. Perfusion ports 25 and 26 are located respectively on first member 20 and second member 21. The second member can be rotated relative to the first member so that the perfusion ports on the first member align with the perfusion ports on the second member.

In use, distal end 2 of the catheter can be inserted directly into a symptomatic carotid artery in the emergency room, after the occlusion is localized with IVUS and regular carotid doppler. The catheter can also be inserted through a guide wire as distal as the occlusion in a cerebral artery, e.g., the ICA, terminal ICA, carotid siphon, MCA, or ACA in an angiogram suite ideally within a few hours of stroke symptom but up to 18 to 24 hours after. Balloon occluder 12 is inflated proximal to the occlusion to create a closed chamber between the occluder and the occlusion. Second member 21 is rotated relative to first member 20 so that perfusion ports 25 and 26 are in complete alignment. High pressure, pulsatile or nonpulsatile perfusion, which involves flow rates of approximately 200 to 300 cc/min, is initiated through lumen 19 and perfusion ports 25 and 26, thereby opening ipsilateral collateral arteries. This enhanced antegrade circulation thus provides improved perfusion to the ischemic area distally and an increased pressure gradient across the occlusion, which may result in dislodgment of the occlusion onto port 6. The more distal the occlusion, the larger the number of potential collateral arteries are available for recruitment, and the higher the likelihood a patient will benefit from the devices and methods. A vasodilator can be infused or vacuum can be applied through lumen 5 and port 6 to reduce pressure in the closed chamber, thereby enhancing retrograde arterial collateral circulation and facilitating dislodgment of the occlusion. The occlusion is removed from the artery by removing the catheter under continuous suction. Focal hypothermia, which has been shown to be neuroprotective, can be administered by perfusing hypothermic oxygenated blood or fluid. Perfusion through perfusion ports 25 and 26 or port 6 distally can be achieved by withdrawing venous blood from a peripheral vein and processing through a pump oxygenator, or by withdrawing oxygenated blood from a peripheral artery, such as a femoral artery, and pumping it back into the carotid artery.

Figure 7A:
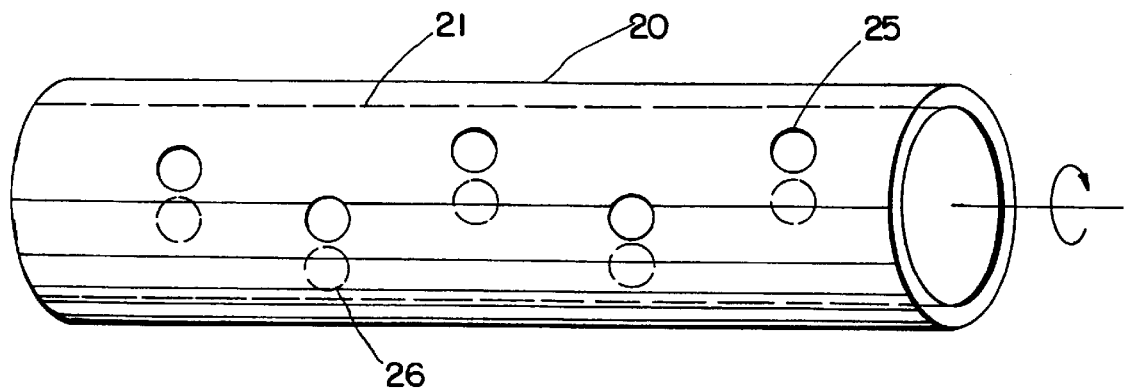
FIG. 7A depicts complete misalignment of the perfusion ports on two cylindrical members.
Figure 7B:
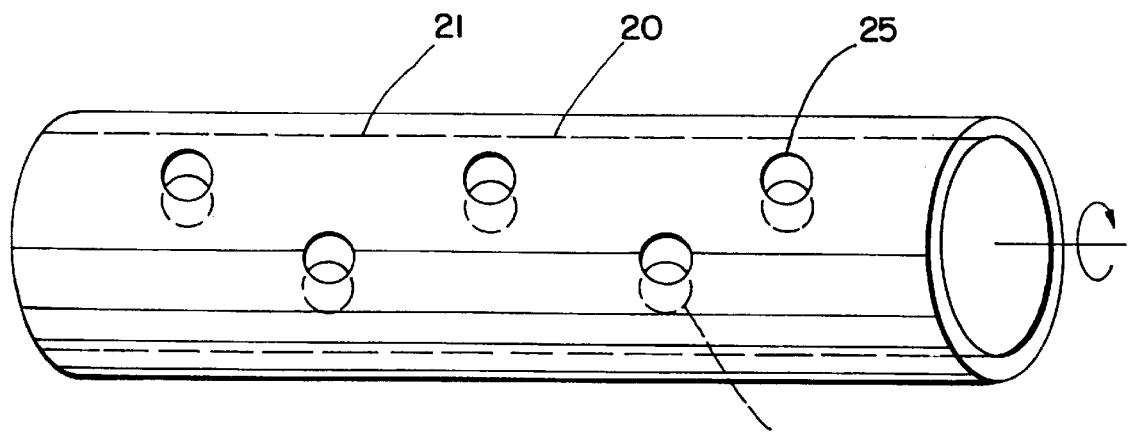
FIG. 7B depicts partial alignment of the perfusion ports on two cylindrical members.
Figure 7C:
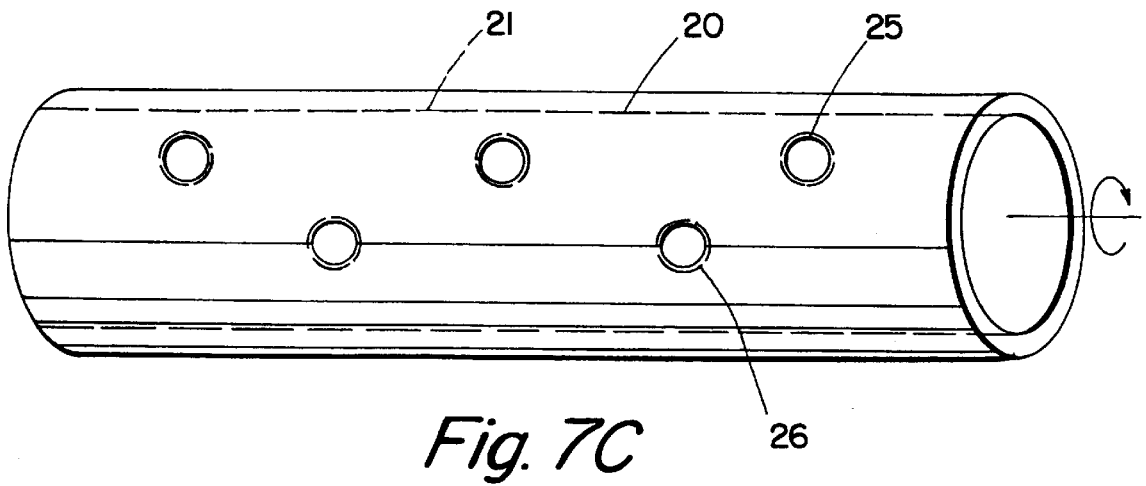
FIG. 7C depicts complete alignment of the perfusion ports on two cylindrical members.

The flow rate of blood through the perfusion ports can easily be controlled by rotating second member 21 relative to first member 20 as depicted in FIGS. 7A, 7B, and 7C. In FIG. 7A, the second member is rotated so that ports 25 and 26 are completely misaligned, thereby achieving no flow through the ports. As second member 21 is rotated clockwise relative to first member 20 in FIG. 7B, ports 26 on the second member become partially aligned with ports 25 on the first member, thereby achieving some flow through the ports. In FIG. 7C, with continuing clockwise rotation of the second member, ports 26 become completely aligned with ports 25, thereby achieving maximum flow through the ports.

Figure 8A:
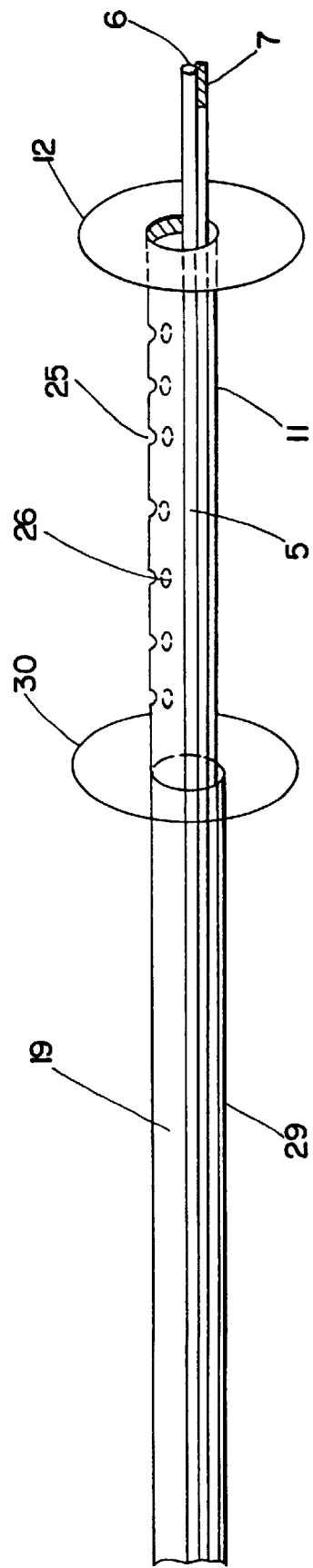
FIG. 8A depicts still another embodiment of the device having two balloon occluders and a chopping mechanism.
Figure 8B:
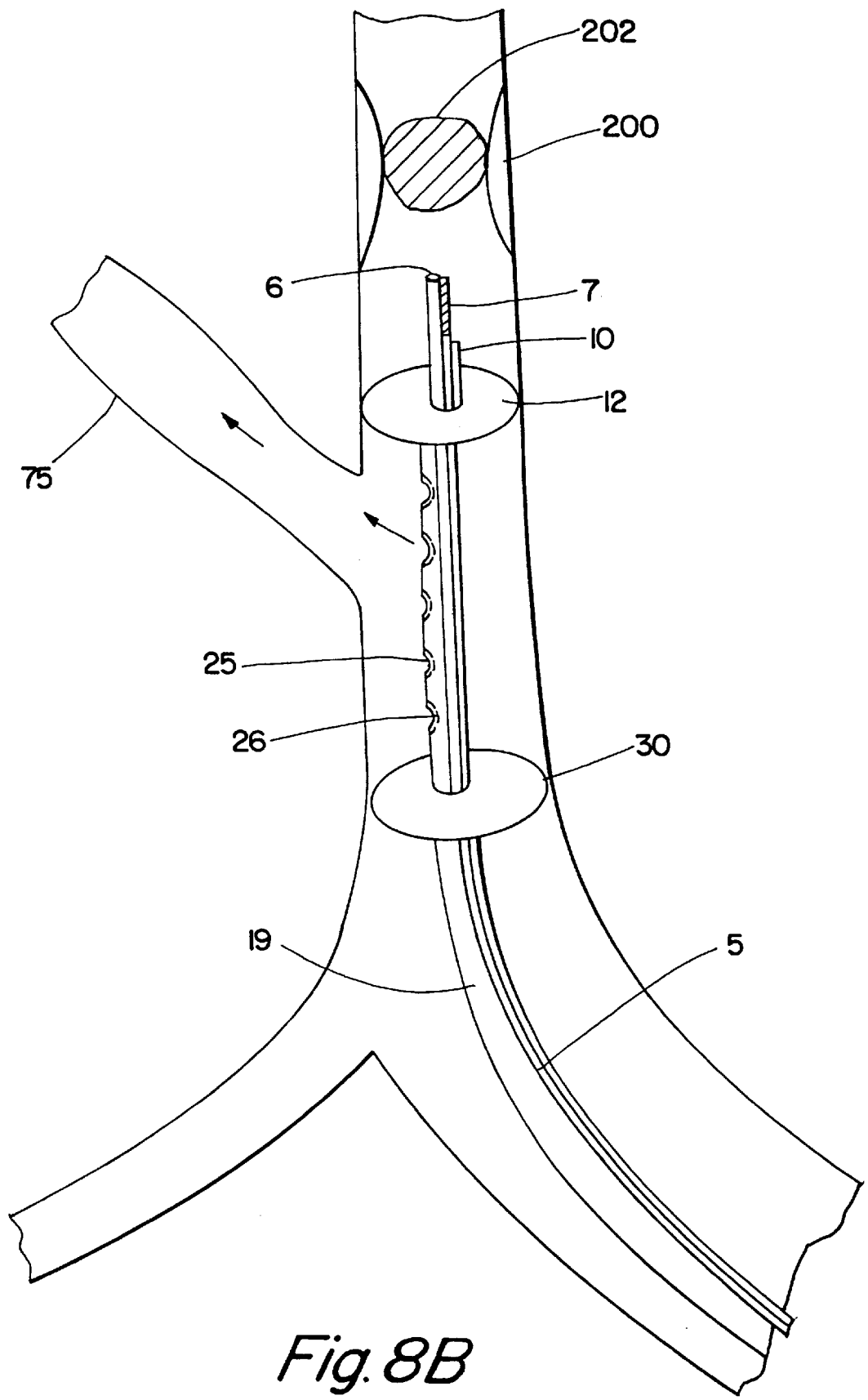
FIG. 8B depicts the device of FIG. 8A inserted proximal to an occlusive lesion.

The device of FIG. 6 may further comprise manometer 10 mounted distal to occluder 12, chopping mechanism 7 associated with port 6 of the catheter, and second balloon occluder 30 as shown in FIG. 8A. Balloon occluder 30 is mounted proximal to the perfusion ports and communicates with inflation lumen 29. In use, a distal end of the catheter is inserted into a cerebral artery and balloon occluder 12 is inflated proximal to occlusion 202 as depicted in FIG. 8B. Balloon occluder 30 is inflated prior to or during high-pressure perfusion of blood through perfusion ports 25 and 26 to reduce run-off of perfused blood proximally, thereby maintaining perfusion pressure to collateral artery 75. When cessation or reduction of perfusion is desired, occluder 30 can be deflated in addition to rotating the second cylindrical member relative to the first member to misalign the perfusion ports. By applying high-pressure perfusion through ports 25 and 26 for antegrade collateral enhancement and suction to lumen 5 and port 6 to reduce pressure within the closed chamber for retrograde collateral enhancement, pressure distal the occlusion is greater than the pressure proximal the occlusion. This pressure differential may dislodge occlusion 202 onto port 6, whereupon the chopping mechanism 7 is automatically or otherwise activated to remove the occlusion. With occluder 30 inflated, occluder 12 may be intermittently deflated and inflated to create alternating negative and positive pressure within the closed chamber, similar to an intra-aortic balloon pump (LABP), to facilitate dislodgment of the occlusion.

If suction fails to dislodge the occlusion, a thrombolytic agent, e.g., t-PA, can be infused through lumen 5 and port 6 to lyse any thrombotic material with greater local efficacy and fewer systemic complications. Administration of thrombolytic agent, however, may not be recommended for devices which are inserted directly into the carotid artery due to increased risk of hemorrhage. If perfusion through ports 25 and 26 are continued for more than a few minutes, removal of excess fluid from the circulation is required to avoid fluid overload. Fluid can be withdrawn from a jugular vein or from any other peripheral vein or artery, e.g., the femoral vein or artery, and re-introduced into the symptomatic artery. Moderate hypothermia, at approximately 32 to 34° C., can be introduced during the fluid recirculation.

Figure 9:
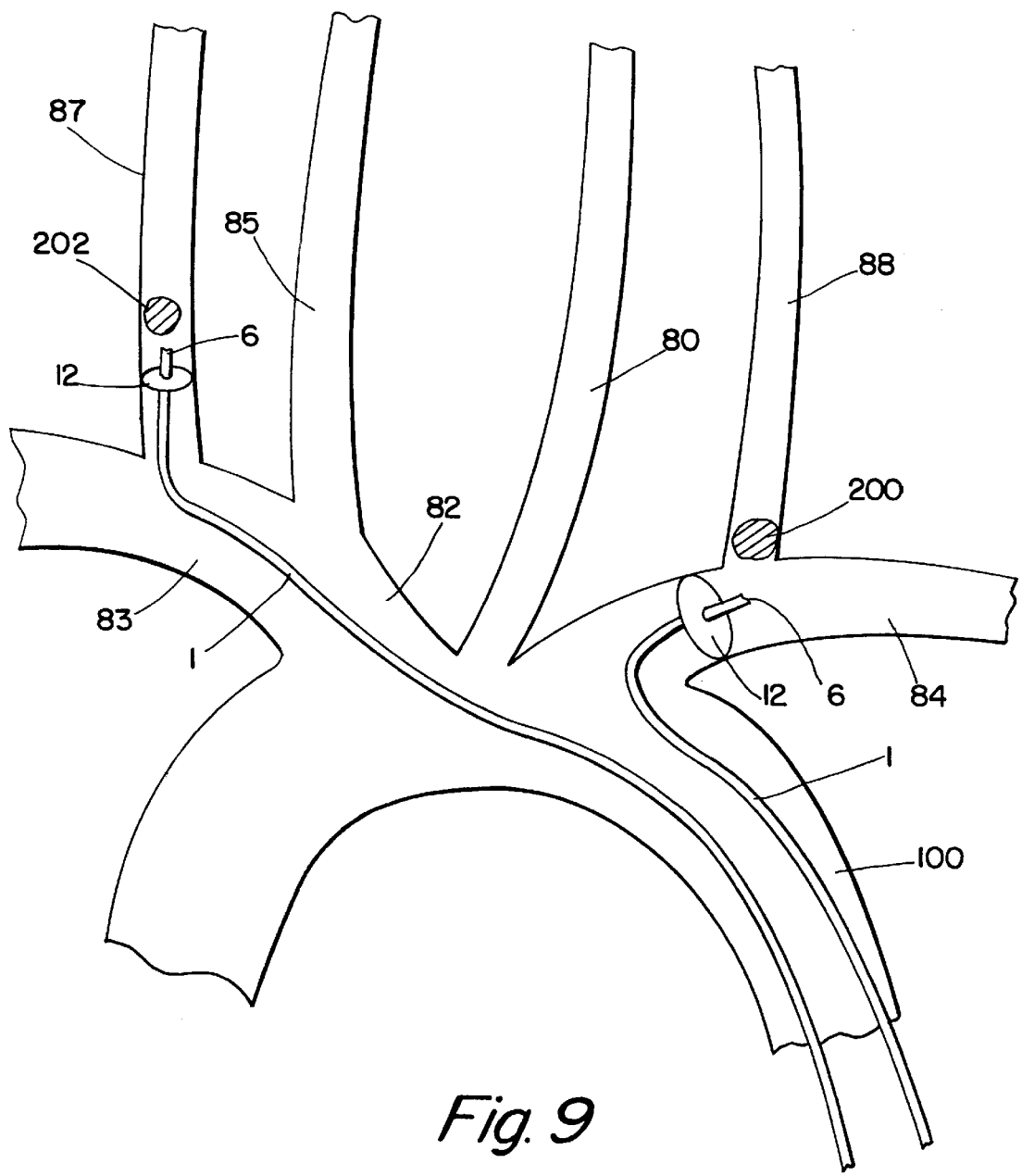
FIG. 9 depicts the device of FIG. 3 inserted into a right vertebral and left subclavian artery.

In patients with vertebral artery occlusions, treatment with angioplasty often results in disastrous complications due to embolization of the occlusive lesion downstream to the basilar artery. Emboli small enough to pass through the vertebral arteries into the larger basilar artery are usually arrested at the top of the basilar artery, where it bifurcates into the posterior cerebral arteries. The resulting reduction in blood flow to the ascending reticular formation of the midbrain and thalamus produces immediate loss of consciousness. The devices described in FIG. 3 and FIG. 6 can be used to (1) remove thromboembolic material from the vertebral artery by utilizing the concept of reversing cerebral blood flow by ipsilateral occlusion, or (2) provide protection during angioplasty and/or stenting by occluding the artery to prevent distal blood flow carrying emboli from progressing through the basilar artery. In using the device of FIG. 3, the occlusion site is first localized with transcranial doppler and angiogram. The catheter can be inserted through an incision on a peripheral artery into the symptomatic vertebral artery or the subclavian artery. In FIG. 9, distal end 6 of catheter 1 is shown inserted proximal to thromboembolic material 202 in right vertebral artery 87 and left subclavian artery 84. Balloon occluder 12 is then inflated to occlude the arterial lumen, thereby reducing flow in the symptomatic vertebral artery. Alternative approaches involve deployment of the occluder positioned in brachiocephalic artery 82, or in subclavian artery 83. In this manner, blood flow is diverted from the contralateral vertebral artery down the symptomatic vertebral artery. When continuous or intermittent suction is applied to the distal end of the catheter, the pressure gradient across the occluding lesion increases and thromboembolic material 202 may be dislodged and captured by the aspiration port. The thromboembolic material may be removed by the chopping mechanism or by removing the catheter under continuous suction, thereby reducing the risk of embolization to the basilar artery.

Figure 10:
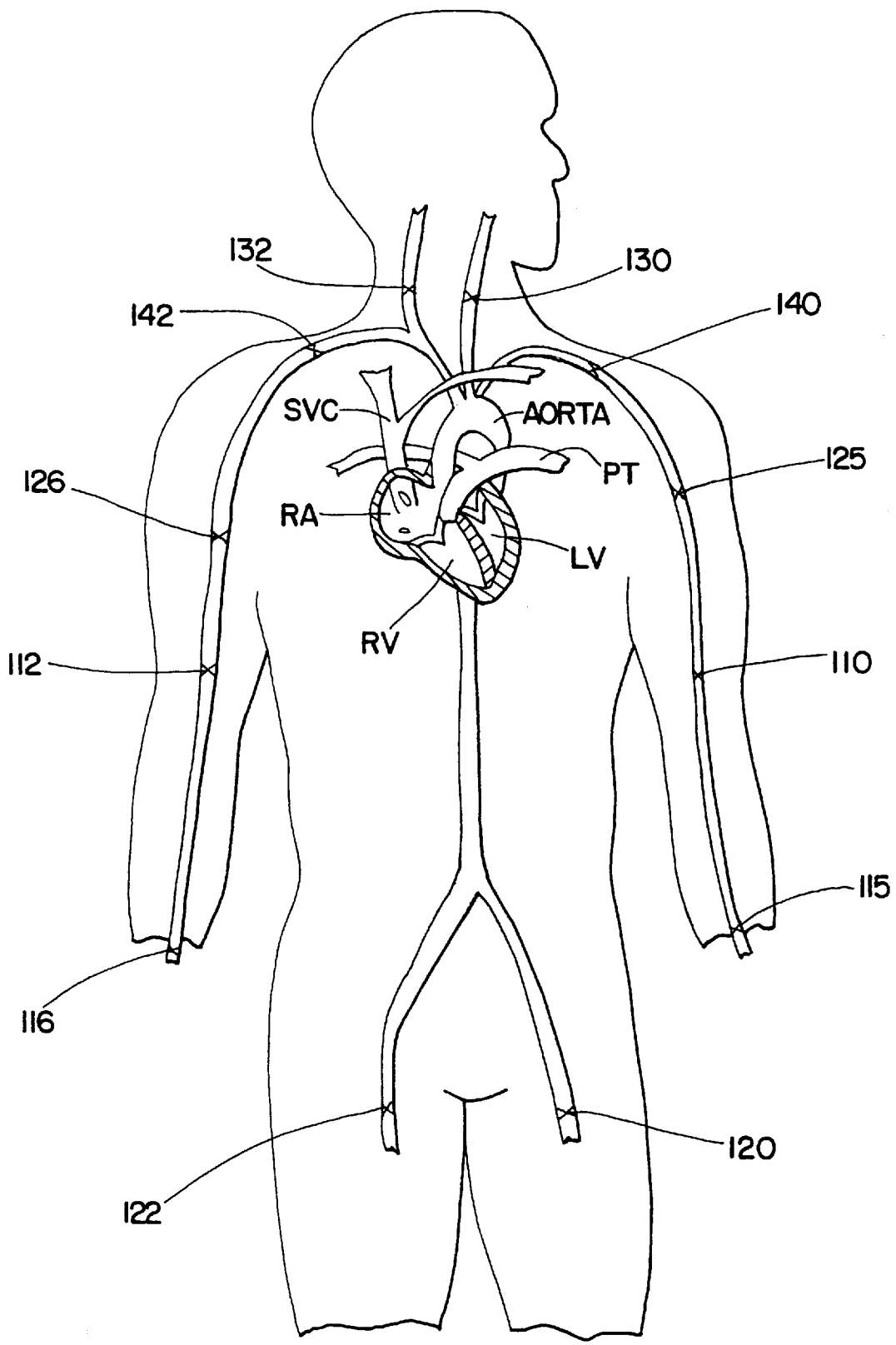
FIG. 10 depicts different peripheral artery access sites for insertion of the device.

FIG. 10 depicts different sites of entry for the devices disclosed herein. An incision can be made on a peripheral artery, such as right femoral artery 122, left femoral artery 120, right radial artery 116, left radial artery 115, right brachial artery 112, left brachial artery 110, right axillary artery 126, left axillary artery 115, right subclavian artery 142, or left subclavian artery. An incision can also be made on right carotid artery 132 or left carotid artery 130 in emergency situations.

The length of the catheter will generally be between 20 to 100 centimeters, preferably approximately between 30 and 60 centimeters. The inner diameter of the catheter will generally be between 0.2 and 0.6 centimeters, preferably approximately 0.4 centimeters. The diameter of the inflated balloon occluder will generally be between 0.3 and 2 centimeters, preferably approximately 0.5 and 1.0 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A medical device for removing thromboembolic material from a carotid artery or any other extracranial or intracranial artery, comprising:

an elongate catheter having a proximal end, a distal end, and a lumen therebetween communicating with an aspiration port at the distal end, the catheter further comprising first and second concentric cylindrical members and a perfusion lumen communicating with one or more perfusion ports, whereby relative rotation of the first and second members causes the perfusion ports on the first member to align with the perfusion ports on the second member;

a balloon occluder mounted on the distal end of the catheter proximal the aspiration port and distal the one or more perfusion ports; and a chopping mechanism associated with the aspiration port, wherein thromboembolic material engaged by suction through the aspiration port is chopped and aspirated through the catheter.

2. The medical device of claim 1, wherein the balloon occluder comprises an elastomeric balloon.

3. The medical device of claim 1, wherein the balloon occluder communicates with a balloon inflation lumen.

4. The medical device of claim 1, wherein the proximal end of the catheter is adapted for attachment to a vacuum.

5. The medical device of claim 1, wherein the aspiration port and lumen are adapted for infusion of fluid, blood, and pharmaceutical agents.

6. The medical device of claim 5, wherein the pharmaceutical agent is a vasodilator.

7. The medical device of claim 6, wherein the vasodilator is selected from the group consisting of nifedipine and nitroprusside.

8. The medical device of claim 5, wherein the pharmaceutical agent is t-PA.

9. The medical device of claim 1, further comprising an additional lumen and port for infusion of blood and pharmaceutical agent.

10. The medical device of claim 1, further comprising a manometer distal to the balloon occluder.

11. The medical device of claim 1, wherein the chopping mechanism comprises an abrasive grinding surface.

12. The medical device of claim 1, wherein the chopping mechanism comprises a rotatable blade which operates within a housing.

13. The medical device of claim 12, wherein the catheter further comprises a second balloon occluder proximal the perfusion ports.

14. A method for removing thromboembolic material from a carotid or cerebral artery, comprising the steps of:

providing a catheter having a proximal end, a distal end, an expandable occluder mounted on the distal end, an aspiration port distal the occluder, an aspiration lumen communicating with the port, and a chopping mechanism;

inserting the distal end of the catheter into the artery;

expanding the occluder to occlude the artery;

applying a negative pressure to the aspiration port, wherein the thromboembolic material is engaged by the port; and operating the chopping mechanism to remove at least a portion of the thromboembolic material.

15. The method of claim 14, wherein the carotid artery is the common carotid artery.

16. The method of claim 14, wherein the carotid artery is selected from the group consisting of the internal carotid artery and carotid siphon.

17. The method of claim 14, wherein the artery is the middle cerebral artery.

18. The method of claim 14, wherein the artery is the anterior cerebral artery.

19. The method of claim 14, wherein the occluder is a balloon which communicates with an inflation lumen.

20. The method of claim 14, wherein the catheter further comprises an additional lumen and port for infusion of blood and pharmaceutical agent.

21. The method of claim 14, wherein chopping mechanism comprises an abrasive grinding surface.

22. The method of claim 14, wherein the chopping mechanism comprises a rotatable blade which operates within a housing.

23. The method of claim 14, further comprising the step of infusing pharmaceutical agent into the carotid artery through the aspiration port.

24. The method of claim 23, wherein the pharmaceutical agent is a vasodilator.

25. The method of claim 24, wherein the vasodilator is selected from the group consisting of nifedipine and nitroprusside.

26. The method of claim 23, wherein the pharmaceutical agent is t-PA.

27. The method of claim 14, further comprising the step of localizing the atheroma with intravascular ultrasound.

28. The method of claim 14, further comprising the step of localizing the thromboembolic material with carotid doppler.

29. The method of claim 14, further comprising the step of localizing the thromboembolic material and direction of flow with transcranial doppler.

* * * * *